United States Patent
Yu et al.

(10) Patent No.: US 6,313,170 B1
(45) Date of Patent: Nov. 6, 2001

(54) L-THREONATE FERROUS, AS WELL AS PHARMACEUTICAL COMPOSITION AND USE FOR IMPROVING AND TREATING HUMAN ANEMIA THEREOF

(76) Inventors: Kai Yu; Zhiwen Wang; Fuping Kou, all of Rm. 602,Unit 6, No. 31 Bldg. Dongwangzhuang Xiaoqu East Rd., Haidiang District, Beijing 100083 (CN)

( * ) Notice: Subject to any disclaimer, the term of this patent is extended or adjusted under 35 U.S.C. 154(b) by 0 days.

(21) Appl. No.: 09/486,569
(22) PCT Filed: Aug. 28, 1998
(86) PCT No.: PCT/CN98/00174
§ 371 Date: Feb. 29, 2000
§ 102(e) Date: Feb. 29, 2000
(87) PCT Pub. No.: WO99/11256
PCT Pub. Date: Mar. 11, 1999

(30) Foreign Application Priority Data

Aug. 29, 1997 (CN) .................................. 97116835

(51) Int. Cl.[7] .................................. A61K 31/19
(52) U.S. Cl. .................................. 514/557; 514/502
(58) Field of Search .................................. 514/502, 557

(56) References Cited

U.S. PATENT DOCUMENTS 5,070,085 * 12/1991 Markham .................................. 514/161
5,174,987 * 12/1992 Takaichi et al. .................................. 424/9

FOREIGN PATENT DOCUMENTS 3-291231   12/1991 (JP) .

OTHER PUBLICATIONS

Equivalent Bioavailability of Iron from Ferrous Salts and a Ferric Polymaltose Complex, P. Jacobs, Arzneim–Forsch. (Drug. Res.) 37(I) Nr. 1a (1987), pp. 113–121.
Effects of So–Called Iron Absorption–Promoting Additives in Humans as Measured with the $^{59}$Fe–Absorption Whole–Body Retention Test, H. C. Heinrich et al., Arzneim.–Forsch. (Drug Res.) 22, Nr. 7 (1972), pp. 1091–1103.
Intestinal Absorption of $^{59}$Fe From Neutron–Activated Commercial Oral Iron(III)–Citrate and Iron (III)–Hydroxide–Polymaltose Complexes in Man, H. C. Heinrich, Arzneim–Forsch. (Drug Res.), 37(I), Nr. 1a (1987), pp. 105–112.
Bovine Ferritin Iron Bioavailability in Man, B. Skikne et al., European Journal of Clinical Investigation (1997) 27, pp. 228–233.
Effects of the Pyrones, Maltol and Ethyl Maltol, On Iron Absorption From the Rat Small Intestine, M. A. Barrand et al., J. Pharm. Pharmacol., 39, 1987, pp. 203–211.
Bioavailability and Therapeutic Efficacy of Bivalent and Trivalent Iron Preparations, J. P. Kaltwasser et al., Arzneim.–Forsch./Drug Res. 37(I), Nr. 1a, 1987, pp. 122–129.
Treatment of Iron Deficiency Conditions in Blood Donors: Controlled Study of Iron Sulphate Versus Iron Protein Succinylate, G. Landucci et al., The Journal of International Medical Research, 15, 1987, pp. 379–382.
Clinical Pharmacokinetics of Iron Preparations, E. Harju, Clin. Pharmacokinet. 17(2), 1989, 69–89.
Assessment of Iron Availability Using Stable $^{54}$Fe, J. P. Kaltwasser et al., European Journal of Clinical Investigation, 21, (1991), pp. 436–442.
Pharmacokinetics of Iron Salts and Ferric Hydroxide–Carbohydrate Complexes, P. Geiser et al., Arzneim–Forsch./Drug Res. 37(1), Nr. 1a (1987), pp. 100–104.
Anti–Anemia Action of Hemin, J. Lin et al., Chinese Journal of Biochemical Pharmaceutics, 1997, pp. 34–36 (English Abstract).
Effect of Sodium Iron Chlorophyllin (SIC) on CFU–E and CFU–GM Yields of Normal and Anemic Animal Models, X. Liu et al., Chin J Hematol, May 1997, vol. 18, No. 5, pp. 234–236 (English Abstract).
Structure/Histotoxicity Relationship of Parental Iron Preparations, P. Geiser et al., Arzneim.–Forsch./Drug Res. 42 (II), Nr. 12 (1992), pp. 1439–1452.

* cited by examiner

Primary Examiner—Dwayne C. Jones
(74) Attorney, Agent, or Firm—Alston & Bird LLP

(57) ABSTRACT

A compound of ferrous L-threonate with structure (I), its compostions and methods useful for iron supplementation for mammals, particularly for human body to improve and treat nutritional iron-deficiency anemia, blood loss anemia and hemolytic anemia.

12 Claims, No Drawings

L-THREONATE FERROUS, AS WELL AS PHARMACEUTICAL COMPOSITION AND USE FOR IMPROVING AND TREATING HUMAN ANEMIA THEREOF

This application is a 371 of PCT/CN98/00174, filed on Aug. 28, 1998.

TECHNICAL FIELDS OF INVENTION

This invention relates to a new derivative of L-threonic acid as a pharmaceutical active compound. More specifically, the invention concerns ferrous L-threonate, a method of making the same, a pharmaceutical composition thereof. In a further aspect, this invention relates to use of ferrous L-threonate for the preparation of a pharmaceutical composition for improving and treating the anemia diseases, particularly, nutritional iron-deficiency anemia (IDA) (hypoferric anemia), blood-loss anemia (hemorrhagic anemia) and hemolytic anemia.

TECHNICAL BACKGROUNDS OF INVENTION

L-threonic acid is one of metabolites of vitamin C. It is reported that some physiological functions of vitamin C were exerted very possibly by some of its metabolites, for example, L-threonic acid and the like. In the other hand, the existing of these compounds could profoundly influence the uptake and utilization of vitamin C.

Calcium L-threonate is a derivative of L-threonic acid. Calcium L-threonate can improve uptake of vitamin C by the lymphoma cells and can be used as the high efficient calcium nutrient for preventing and treating varied diseases caused by calcium deficiency (Chinese Patent, ZL 96 06507.9). Also, calcium L-threonate is useful for allaying inflammation and reducing blood pressure. But there was no report for other salts of L-threonic acid and their use as drugs on treating diseases.

Anemia is a common disease, which is caused by a various reasons. Their reasons mainly include: (1) a decrease of red blood corpuscle (RBC) in volume or in quantity; (2) a decrease of hemoprotein in amount due to chronic or acute blood loss and the injury of RBC due to its exposing to some chemical compounds; and (3) a reduction of the number of produced RBC due to deficiency of marrow or such nutrients as ferrous and vitamin $B_{12}$ used to produce RBC.

Nutritional iron-deficiency anemia (IDA) is a very common case among anemia diseases. The reason is that the body iron balance between excretion and storage has not been sustained. Consequently, there was more and more excretion but less and less storage of body iron with time. These phenomena often happened during the periods of growth, pregnancy and chronic blood loss due to various reasons. For example the less intake of iron from food is an important factor to lead to iron deficiency for body.

In fact, the nutritional IDA is a worldwide nutritional problem. For treating this kind of disease, simply taking iron-rich foods is hard to have good effects compared with using drugs. Among IDA drugs of iron preparations, ferrous sulfate is a relative popular drug with good effectiveness, low price and abundant resource. Even so, the extensive application of ferrous sulfate for treating IDA is limited because of its side effects (Chinese Child Blood, Vol. 1, p24–26, 1996). Therefore, it is desirable to provide new active compounds and compositions thereof for improving and treating IDA very efficiently.

Blood-loss anemia is a usual case of anemia. Most patients are women in the periods of pregnancy and menses.

Another anemia is hemolytic anemia. It is mainly caused by the following reasons: exposing to hemolytic chemical materials such as naphthalene and sulfanilamide; production of antibody in cells due to administration of drugs; and presence of cells with hereditary defection in body. A method for treating hemolytic anemia is to remove those harmful chemical reagents from body. Therefore, it is desirable to provide an active compounds and compositions thereof so as to improve and treat hemolytic anemia. It is in particularly desirable to provide an active compound and composition thereof so as to improve and cure these three kinds of anemia diseases.

OBJECT OF INVENTION

It is one object of this invention to provide a new derivative of L-threonic acid, in particularly, ferrous L-threonate.

It is another object of the invention is to provide compositions containing ferrous L-threonate for improving and treating such anemia as nutritional IDA, blood-loss anemia and hemolytic anemia.

It is a further object of the invention is to provide a method for improving and treating these anemia diseases.

ADVANTAGE OF INVENTION

Ferrous L-threonate of this invention has higher absorption rate compared with known iron preparations, for example, ferrous sulfate. Under the same dosages (element Fe/kg body weight) and the same body situation, animal test results showed that ferrous L-threonate was absorbed with higher absorptivity than ferrous sulfate. It is used safely and without toxicity. As iron preparation, ferrous L-threonate can significantly improve and cure hemolytic anemia, blood-loss anemia and nutritional IDA with the characters of high bioavailability and controlled release, compared with ferrous gluconate and ferrous fumarate. Ferrous L-threonate can be taken as both good iron supplement and drug for improving and treating anemia disease.

DETAIL DESCRIPTION OF INVENTION

This invention concerns the compound so-called ferrous L-threonate with chemical structure given as below.

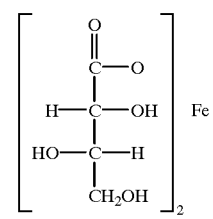

Ferrous L-threonate has L-form optical structure. It is stable, soluble in water and exists mainly as the complex form in its solution.

Preparation methods for ferrous L-threonate:
1. Prepared by neutralization reaction of L-threonic acid with ferrous oxides or ferrous hydroxides, for example, with ferrous oxide (FeO) and ferrous hydroxide (Fe (OH)$_2$);
2. Prepared by replacement reaction of L-threonic acid or calcium L-threonate with inorganic ferrous salts, such as ferrous sulfate (FeSO$_4$), ferrous chloride (FeCl$_2$) and ferrous nitrate (Fe(NO$_3$)$_2$), wherein L-threonic acid can be obtained by oxidizing vitamin C or by removing calcium from calcium L-threonate.

Ferrous oxides, ferrous hydroxides and inorganic ferrous salts can be prepared from the corresponding ferric compounds, such as, ferric nitrate, ferric sulfate and Fe3O4. If L-threonic acid is available in the market, it also can be used to prepare ferrous L-threonate according to the methods described above.

The reaction conditions for preparing ferrous L-threonate are, (1) Under pH 6–10, preferably at pH 7–9, vitamin C was oxidized by oxidant, for example, by hydrogen peroxide solution to get a solution of L-threonic acid, (2) Under the protection of inert gas such as nitrogen gas, the solution of L-threonic acid reacts with ferrous compounds, such as ferrous oxides, ferrous hydroxides and ferrous salts to produce ferrous L-threonate.

This invention also relates to compositions containing ferrous L-threonate as therapeutically active component. The composition also can include other therapeutically active compounds, pharmaceutically acceptable carrier and such medical supplementary materials as flavours, excipients and vitamins. Preferably, the composition of the invention contains ferrous L-threonate, vitamin C or vitamin B12, of which the weight ratio of ferrous L-threonate is 10–90%, preferred range is 30–80% and more preferred range is 40–60%.

The definition of the term "pharmaceutically acceptable" is that from the view of the point of pharmacy, those materials or components and their properties are acceptable by patients and pharmacists with stability and bioavailability.

The ferrous L-threonate of the invention can be prepared as any forms of drug. These forms include tablet, capsule, suppository, liquid, suspending agent, syrup, emulsion, gel, ointment, freeze-dried powder, pill, film, lipoplast, dispersible micro-powder and injection solution. Solid forms of tablet and powder are preferred.

According to the invention, the tablet can be prepared by mixing the active compound, ferrous L-threonate with excipients like calcium carbonate, calcium phosphate and lactose, with disintegrating agent like corn starch, with cohesive materials like starch and gelatin, with lubricants like magnesium stearate and talc powder, and with some controlled release materials like carboxypolymethylene and carboxymethyl cellulose.

Inner tablets used for preparing sugarcoating tablets can be made in the similar methods described above. Sugarcoating materials are insect glue, arabic gelatin, talc titanium dioxide and so on. Usually, several-layer technique was employed to prepare the inner tablets to avoid the incompatible properties possibly caused by different components used.

Injection solution can be prepared according to the common technology. Similarly, other forms of drug for ferrous L-threonate's composition can be prepared in terms of the known techniques and methods.

Ferrous L-threonate can be taken as nutritional additive to food and to beverage to enhance the uptake quantity of iron by body and thus to improve and cure anemia disease.

The invention provides methods for improving and treating such anemia as nutritional IDA, blood-loss anemia and hemolytic anemia by ferrous L-threonate and/or its compositions.

In a further respect, the methods of the invention need patients to take a certain quantity of ferrous L-threonate.

According to methods of the invention, methods are available to animal, such as bull, horse and sheep and especially to human being including child, woman and old people, and particularly to child and woman.

Different ways of administration, such as oral, injecting and so on, do not influence the activity and effectiveness of ferrous L-threonate.

According to methods of the invention, the dosages for treating anemia will vary in terms of patient conditions and administration ways used in practice. To determine the accurate dosage needs to consider the anemia's extent, patient's age, body weight and so on. For instance, the dosage for children should be less than that for adult.

On using solid form of drug, the quantity of ferrous L-threonate for adult is usually in the range of 10 mg–1 g a day. Preferred range is 20 mg–800 mg a day, more preferred range 30 mg–500 mg a day, for example, 30 mg, 250 mg or 400 mg, far more preferred range 50 mg–200 mg a day, for example, 60 mg or 100 mg or 150 mg.

For animal, particularly for mammal except human being, the dosage of ferrous L-threonate depends on the experimental results for the different races of animals.

The methods of the invention for improving and treating anemia are usable for nutritional IDA, blood-loss anemia and hemolytic anemia.

More specifically, the methods are suitable to growth period for children, pregnancy and menses periods for women, the case of chronic or acute blood loss and the case of insufficient uptake of iron from food.

The methods of the invention also can be used to the case of hemolytic anemia developed by RBC damage and decrease of RBC number when RBC exposes to some chemical reagents, for example.

This invention also relates to the functions of ferrous L-threonate as supplementary drug under some conditions, to treat the whole body system disorder caused by, for instance, iron deficiency.

In terms of evaluation program of food safety and toxicology, Horn method cited in the published standard of GB15193.4-94 was adopted to evaluate the acute toxicity of ferrous L-threonate with the results of $LD_{50}$ 3.16 g/kg and 3.69 g/kg for female and male rat, respectively. This fact illustrated that the toxicity of ferrous L-threonate belongs to the grade of very lower.

According to the published standards of GB15193.4-94, GB15193.5-94, GB15198.4-94 and GB15193.14-94, the Ames test, micronucleus test of bone marrow cells and chromosome aberration test of mice testicle cells have been carried out and all tests' results are negative. Oral administration of ferrous L-threonate did not produce embryonic toxicity and abberation.

The invention supplies the digestive absorption study of ferrous L-threonate on male Wistar rat (see experiment 1).

This invention also describes the pharmacodynamics studies of ferrous L-threonate for hemolytic anemia model, nutritional IDA model and blood-loss anemia model on rats (see experiment 2).

This invention further gives the clinical investigation of ferrous L-threonate for improving IDA disease of children (see experiment 3).

EXPERIMENT 1

Metabolic and Absorption Study of Ferrous L-threonate on Male Wistar Rats

Drugs: Ferrous L-threonate was supplied by Beijing Juneng Asia-Pacific Life Science Research Center. It is yellow-green powder and soluble in water and contains element ferrous 15.47%. Its chemical formula is $Fe(C_4H_7O_5)_2 \cdot 2H_2O$, molecular weight:362.

Animals: Male Wistar rats were supplied by Experimental Animal Center, Tumor Institute of Heilongjian Province with body weight of 140 g–180 g. The iron-low diet contains iron 0.9 mg/kg.

Methods 50 rats were randomly divided into 5 groups of [19] 10 rats each. On this basis of administration of iron-low diet, each group of rats was administered respectively by gavage according to the dosage below:

High dosage group: Fe, 5 mg/kg, ferrous L-threonate, 32.32 mg/kg;

Middle dosage group: Fe, 2.5 mg/kg, ferrous L-threonate, 16.16 mg/kg;

Low dosage group: Fe, 1.0 mg/kg, ferrous L-threonate, 6.46 mg/kg;

Positive drug control group (ferrous sulfate): Fe, 2.5 mg/kg, ferrous sulfate, 12.43 mg/kg;

Negative drug control group (iron-low diet): Fe, 0.9 mg/kg (measured value).

After the end of 7 days feeding normal diet period, rats were supplemented with iron-low diet prepared according to AOAC formula for another 7 days. The 1–3 groups were treatment groups and supplemented with ferrous L-threonate 32.32 mg/kg (5 mgFe/kg, high dose group), 16.16 mg/kg (2.5 mg Fe/kg, middle dose group) and 6.46 mg/kg (1.0 mg Fe/kg, low dose group), respectively. The forth, positive drug control group, was provided with ferrous sulfate 12.43 mg/kg (2.5 mg Fe/kg). The fifth was model control group and was offered with iron-low diet (0.9 mg Fe/kg). Each groups were arranged to take drug one time by I.G (gavage) method per day and in the same time were supplemented with deionized water.

The test was sustained three days. Each rat's excrement was collected, dried at temperature 80–90° C., weighed and ground into 40–60 meshes. About 0.5 to 0.6 gram sample was taken and a mixture of nitric acid and perchloric acid at a ratio of 4:1 was added therein until completion of digestion. The constant volume is 10 ml. The iron content of excrement was determined by atomic absorption method and the iron absorptive rate for each rat can be calculated by the formula listed below.

$$\text{Digestive absorptivity (\%)} = \frac{\text{Quantity of iron intake} - \text{Quantity of iron excrement}}{\text{Quantity of iron intake}} \times 100$$

Results: The tests results were listed in Table 1 and it indicated that the digestive absorptivity of ferrous L-threonate is significantly higher compared with that of ferrous sulfate (P<0.01) in the condition of same ferrous dosage.

TABLE 1

Digestive absorptivity for different ferrous salts

| Groups | Samples | Dosage (mg Fe/kg) | Absorptivity (%) |
|---|---|---|---|
| High dosage of ferrous L-threonate | 10 | 5 | 42.60 ± 1.79 |
| Middle dosage of ferrous L-threonate | 10 | 2.5 | 54.90 ± 4.08* |
| Low dosage of ferrous L-threonate | 10 | 1 | 59.10 ± 5.01 |
| Ferrous sulfate group | 10 | 2.5 | 42.00 ± 1.02 |
| Model group | 10 | 0.9 | 55.50 ± 1.85 |

EXPERIMENT 2

Pharmacodynatics of Ferrous L-threonate for Hemolytic Anemia Model, Nutritional IDA Model and Blood-loss Anemia Model 1. Drugs: Ferrous L-threonate, yellow-green powder and 15.47% ferrous content, was supplied by Beijing Juneng Asia-Pacific Life Science Research Center. Ferrous gluconate, the positive control drug, yellow-green powder and 11% ferrous content, was purchased from Ganjian Pharmaceutical Company of Jianxi Province. Ferrous fumarate, 6.4% ferrous content, was purchased from the 18th Pharmaceutical Company of Shanghai. All drugs were diluted by distilled water.
2. Testing animal and division of group Male Wistar rats (Animal Center of Beijing Medical University) with body weight 250±10 g were kept under controlled conditions and supplemented with normal diet and water. Animal diet also was purchased from Beijing Medical University.
(1) Hemolytic Anemia Model: Hemolytic anemia model was prepared for rats by injecting reagent of acetylphenylhydrazine ($C_8H_{10}N_2O$, produced by Beijing Biochemical Company) subcutaneously. The drug acetyphenylhydrazine was mixed with physiological saline to get its injection solution of 4% by weight of acetyphenylhydrazine. The solution was injected subcutaneously into each rat with a dosage of 57 $\mu g/g$ at the beginning of the experiments. The content of blood hemochrome for each rat was examined at 2 days and 4 days later, respectively. When the mean blood hemochrome decreased to about 6.11±0.25 g %, rats were randomly divided into 6 groups of 18 rats each. The 1–3 groups were treatment groups of ferrous L-threonate with high, middle and low dosages. The forth groups was positive drug control groups. The fifth group and the sixth group were designed as model group and normal control group, respectively.
(2) Nutritional Anemia Model: Male Wistar rats with body weight 43±2.5 g (Animal Center of Beijing Medical University) were randomly divided into 8 groups of 10 rats each, wherein 6 groups were established for the investigation of nutritional anemia and 2 groups were used as normal control group. The rats of these six groups were supplemented with iron-low diet (prepared according to the formula of AOAC, iron content 8.0 mg/kg) and deionized water four weeks to prepare the nutritional IDA model, which also was called hemoglobin exhausting test. Another two groups were designed as normal control groups and were provided with normal diet (obtained from Beijing Medical University) and water during the whole experimental period.

Hemoglobin of each group of rats was measured one time every 7 days. After the end of 4 weeks of feeding iron-low diet period, the content of hemoglobin of nutritional IDA groups' rats reduced to about 7.51±0.17 g and in that time the blood index of one nutritional IDA group and one normal control group were determined as index of before treatment by drug. Other 6 groups (three for ferrous L-threonate, one for ferrous gluconate, one for mode control and one normal control group) rats were kept under controlled conditions (ambient temperature 23° C., 60% relative humidity, and 10 hours light) in animal feeding room to continue the further test.

(3) Blood-loss Anemia Model: 120 male Wistar rats (Animal Center of Beijing Medical University) with body weight 130±8.2 g were randomly divided into 8 groups of 15 rats each. 7 groups were prepared as hemolytic anemia groups and one group was taken as normal control group supplemented with normal diet and water. The hemolytic anemia model was prepared by subjecting rats to inner canthus bloodletting of right eye through capillary glass tube. The first bloodletting content was 2.0 ml for each rat and in that time the range of hemochrome for rats was from 9.78 to 10.65 g %. Two days later, the second bloodletting (2 ml/rat) was carried out with the hemochrome values of 7.40–7.88 g %. The total bloodletting volume for each rat was 4 ml and was 32.9% in volume of the whole blood circulating the body.

While one hemolytic anemia group and one normal control group were taken as reference groups compared with other groups left. These two groups' rats were killed and the blood parameters were recorded. Other six groups now were randomly divided into three treatment groups of ferrous L-threonate with high, middle and low dosages respectively, two positive drugs control groups of ferrous gluconate and ferrous fumarate and one model group. At the end of 12 days and 18 days experimental periods, 5 and 10 rats of each group were killed correspondingly. During the course of experiment, the variations of hemochrome content were examined with 6 days interval.

Dosages: Three treatment groups of ferrous L-threonate were divided into high dosage group with element ferrous 17.28 mg/kg, middle dosage group with element ferrous 8.64 mg/kg and low dosage group with element ferrous 4.32 mg/kg. While Element ferrous content 8.64 mg/kg as ferrous gluconate or ferrous fumarate was for positive drug control group. The groups for blood-loss anemia were provided iron-low diet and deionized water during the period of the administration of drugs, while the normal animal control group was provided normal diet and deionized water.

Test Results: The index of anemia were investigated for the cases of before anemia model preparation, after anemia model preparation, one, two or three weeks after treatment of drugs.

(1) Results for Hemolytic Model Study

TABLE 2

Variations of hemoglobin content of groups (g %) after two weeks of administration of drugs

| Groups | Before anemia | After anemia | One week after treatment | Two weeks after treatment |
| --- | --- | --- | --- | --- |
| High dosage of ferrous L-threonate | 14.9 ± 0.422 | 6.18 ± 0.419 | 11.95 ± 0.844 | 14.34 ± 0.420 |
| Middle dosage of ferrous L-threonate | 15.01 ± 0.421 | 5.87 ± 0.590 | 11.11 ± 0.633 | 14.04 ± 0.383 |
| Low dosage of ferrous L-threonate | 14.89 ± 0.501 | 5.94 ± 0.526 | 9.95 ± 0.488 | 12.57 ± 0.590 |
| Ferrous gluconate group | 15.34 ± 0.352 | 6.57 ± 0.503 | 10.62 ± 0.530 | 12.65 ± 0.364 |
| Model group | 15.03 ± 0.352 | 6.01 ± 0.503 | 8.14 ± 0.530 | 10.79 ± 0.364 |
| Normal control group | 14.60 ± 0.302 | 14.23 ± 0.434 | 14.33 ± 0.526 | 14.21 ± 0.354 |

TABLE 3

Results of RBC counts (× $10^{12}$/L)

| Groups | Before anemia | After anemia | Two weeks after treatment |
| --- | --- | --- | --- |
| High dosage of ferrous L-threonate | 7.185 ± 0.292 | 2.310 ± 0.248 | 5.663 ± 0.236 |
| Middle dosage of ferrous L-threonate | 7.238 ± 0.181 | 2.163 ± 0.422 | 5.376 ± 0.273 |
| Low dosage of ferrous L-threonate | 8.290 ± 0.188 | 3.370 ± 0.193 | 4.863 ± 0.136 |
| Ferrous gluconate group | 7.215 ± 0.212 | 2.188 ± 0.201 | 5.011 ± 0.337 |
| Model group | 8.180 ± 0.277 | 3.323 ± 0.384 | 3.647 ± 0.293 |
| Normal control group | 7.160 ± 0.251 | 7.132 ± 0.324 | 7.202 ± 0.336 |

TABLE 4

Results of blood granulophilocyte counts (%)

| Groups | Cells for counting | Before anemia | After anemia | Two weeks after treatment |
| --- | --- | --- | --- | --- |
| High dosage of ferrous L-threonate | 1000 | 1.193 ± 0.093 | 94.80 ± 1.183 | 6.11 ± 1.375 |
| Middle dosage of ferrous L-threonate | 1000 | 1.138 ± 0.198 | 95.35 ± 2.026 | 7.60 ± 0.551 |
| Low dosage of ferrous L-threonate | 1000 | 1.298 ± 0.147 | 95.475 ± 1.575 | 9.35 ± 1.089 |
| Ferrous gluconate group | 1000 | 1.448 ± 0.139 | 96.00 ± 2.174 | 9.12 ± 0.966 |
| Model group | 1000 | 1.135 ± 0.256 | 97.85 ± 1.790 | 19.21 ± 3.063 |
| Normal control group | 1000 | 1.602 ± 0.154 | 1.734 ± 0.253 | 1.932 ± 0.387 |

The results listed in table 2–4 showed that by treating two weeks, the items of RBC and hemochrome for all iron supplementation groups increased significantly compared with those of before treatment, the blood granulophilocyte counts lowered than treatment before, while the cases of high and middle dosages of ferrous L-threonate were similar to those of normal control group. In contrast to drugs groups, model group behaved relative weak effects on curing anemia and this in fact was reasonable. Under the same dosage of iron (8.64 mg/kg), the actions of ferrous L-threonate on treating anemia was considerably better than ferrous gluconate.

TABLE 5

Contents of whole blood iron and serum ferritin (SF)

| Groups | Iron content of whole blood (µg/ml) | Serum ferrintin ng/ml |
|---|---|---|
| Before anemia | 361.89 ± 20.841 | 23.60 ± 1.94 |
| After anemia | 178.81 ± 14.849 | 9.52 ± 1.61 |
| High dosage of Ferrous L-threonate | 326.95 ± 26.956 | 24.05 ± 1.74 |
| Middle dosage of ferrous L-threonate | 301.89 ± 19.500 | 23.54 ± 2.50 |
| Low dosage of Ferrous L-threonate | 283.53 ± 23.051 | 19.38 ± 1.57 |
| Ferrous gluconate | 286.04 ± 26.797 | 20.14 ± 2.83 |
| Model group | 198.11 ± 17.122 | 13.70 ± 0.95 |
| Normal control group | 333.11 ± 17.35 | 23.48 ± 1.82 |

The results from table 5 showed that in comparison with model group, the contents of whole blood iron and serum ferritin for all groups of drugs treatment enhanced significantly ($P<0.01$) while variations of these items for ferrous L-threonate groups except low dosage group were more considerably better than those of ferrous gluconate group.

(2) Results for Nutritional IDA Model Study

The exhaustive hemoglobin test of rat was 28 days period and the results were listed in table 6 and table 7.

TABLE 6

Hemoglobin exhausting test for rats supplemented with iron-low diet
n = 10 (g %)

| Groups | 7-day | 14-day | 21-day | 28-day |
|---|---|---|---|---|
| High dosage group with low-iron diet | 11.19 ± 0.41 | 10.28 ± 0.48 | 9.03 ± 0.75 | 7.82 ± 0.37 |
| Middle dosage group with low-iron diet | 11.33 ± 0.38 | 10.14 ± 0.57 | 9.06 ± 0.83 | 7.51 ± 0.57 |
| Low dosage group with low iron diet | 11.18 ± 0.41 | 10.82 ± 0.35 | 8.45 ± 0.53 | 7.36 ± 0.58 |
| known drug with low iron diet | 10.87 ± 0.45 | 10.44 ± 0.48 | 8.64 ± 0.39 | 7.34 ± 0.46 |
| control group with low-iron diet | 11.35 ± 0.60 | 10.08 ± 0.69 | 8.74 ± 0.73 | 7.53 ± 0.60 |
| control group with normal diet | 11.60 ± 0.46 | 12.30 ± 0.42 | 12.85 ± 0.57 | 13.76 ± 0.30 |

TABLE 7

Results of RBC, blood granulophilocyte (GPC) counts, blood iron content and SF of hemoglobin exhausting test

| Groups | RBC (× $10^{12}$/L) | GPC (%) | Blood iron (µg/ml) | SF (ng/ml) |
|---|---|---|---|---|
| Normal diet group | 6.654 ± 0.46 | 3.41 ± 0.32 | 313.11 ± 7.35 | 23.48 ± 1.82 |
| The sixth iron-low diet group | 2.82 ± 0.41 | 11.96 ± 0.88 | 168.63 ± 23.21 | 12.99 ± 1.61 |

TABLE 8

Variations of hemochrome content for IDA rats after treatment
n = 10 g %

| Groups | 7-day | 14-dat | 21-day |
|---|---|---|---|
| Normal control group | 13.70 ± 0.32** | 13.84 ± 0.22** | 13.98 ± 0.39** |
| Model group | 7.92 ± 0.61 | 7.77 ± 0.44 | 8.31 ± 0.51 |
| High dosage of ferrous L-threonate | 10.52 ± 0.49* | 12.23 ± 0.45** | 13.67 ± 0.41** |
| Middle dosage of ferrous L-threonate | 10.12 ± 0.66* | 11.46 ± 0.36* | 12.98 ± 0.38** |
| Low dosage of ferrous L-threonate | 8.74 ± 0.44 | 10.76 ± 0.37* | 11.87 ± 0.50** |
| Ferrous gluconate group | 9.08 ± 0.65 | 11.66 ± 0.54* | 12.40 ± 0.58** |

*$P < 0.05$
**$P < 0.01$ compared with model group

TABLE 9

RBC, GPC, SF and blood iron for IDA rats after treatment 21 days
n = 10

| Groups | RBC (× $10^{12}$/L) | GPC (%) | Blood iron (µg/ml) | SF (ng/ml) |
|---|---|---|---|---|
| Normal control group | 7.197 ± 0.28 | 2.30 ± 0.35 | 308.54 ± 17.38 | 24.2 ± 1.06 |
| Model group | 3.273 ± 0.23 | 12.30 ± 0.87 | 200.31 ± 28.78 | 13.1 ± 1.45 |
| High dosage of ferrous L-threonate | 6.564 ± 0.65 | 2.29 ± 0.54 | 304.37 ± 14.12 | 23.40 ± 1.50 |
| Middle dosage of ferrous L-threonate | 6.116 ± 0.21 | 2.63 ± 0.76 | 302.02 ± 18.92 | 20.88 ± 1.53 |
| Low dosage of ferrous L-threonate | 5.957 ± 0.44 | 4.18 ± 1.12 | 290.78 ± 20.13 | 17.98 ± 1.34 |
| Ferrous gluconate group | 6.286 ± 0.36 | 2.36 ± 0.79 | 297.50 ± 14.82 | 20.39 ± 2.10 |

The results of table 8 showed that the hemochrome content of IDA rats treated by ferrous L-threonate started to increase at the end of 7 days supplementation, and reached nearly the normal levels of normal control groups.

RBC, whole blood iron content and SF for drug treatment groups (see table 9) increased considerably, while the blood granulophilocyte counts of these groups decreased compared with the model control group. Further, under the same ferrous dosage the situations of parameters investigated were better than those of the known drug, ferrous gluconate, which suggested that ferrous L-threonate has better effects on improving and treating nutritional IDA.

(3) Results for Blood-loss Model Study

TABLE 10

Blood hemochrome content for rats with blood-loss anemia
n = 10

| Groups | Before treatment | 6 days after treatment | 12 days after treatment | 18 days after treatment |
|---|---|---|---|---|
| High dosage of ferrous L-threonate | 7.88 ± 0.28 | 8.70 ± 0.43 | 11.01 ± 0.34 | 12.40 ± 0.63 |
| Middle dosage of ferrous | 7.40 ± 0.54 | 8.35 ± 0.21 | 10.67 ± 0.37 | 12.14 ± 0.27 |

TABLE 10-continued

Blood hemochrome content for rats with blood-loss anemia
n = 10

| Groups | Before treatment | 6 days after treatment | 12 days after treatment | 18 days after treatment |
|---|---|---|---|---|
| L-threonate Low dosage of ferrous L-threonate | 7.61 ± 0.53 | 8.00 ± 0.42 | 10.20 ± 0.49 | 11.26 ± 0.79 |
| Ferrous gluconate group | 7.50 ± 0.76 | 7.95 ± 0.30 | 10.50 ± 0.61 | 11.80 ± 0.63 |
| Ferrous fumarate group | 7.43 ± 0.85 | 7.80 ± 0.24 | 10.12 ± 0.52 | 11.84 ± 0.45 |
| Model group | 7.51 ± 0.63 | 7.42 ± 0.26 | 9.03 ± 0.56 | 10.39 ± 0.46 |

TABLE 11

Variations of RBC and GPC after treatment n = 10

| Groups | RBC ($\times 10^{12}$/L) 12 days | RBC ($\times 10^{12}$/L) 18 days | GPC (%) 12 days | GPC (%) 18 days |
|---|---|---|---|---|
| High dosage of ferrous L-threonate | 5.67 ± 0.313 | 5.84 ± 0.199 | 10.04 ± 0.97 | 7.84 ± 0.871 |
| Middle dosage of ferrous L-threonate | 4.810 ± 0.178 | 5.21 ± 0.194 | 12.58 ± 1.54 | 8.44 ± 0.753 |
| Low dosage of ferrous L-threonate | 4.242 ± 0.128 | 4.76 ± 0.228 | 13.12 ± 1.84 | 8.91 ± 1.277 |
| Ferrous gluconate group | 4.488 ± 0.271 | 5.14 ± 0.342 | 12.66 ± 2.04 | 9.04 ± 0.793 |
| Ferrous fumarate group | 4.200 ± 0.271 | 5.14 ± 0.342 | 12.66 ± 2.04 | 9.04 ± 0.793 |
| Model group | 4.046 ± 0.147 | 4.37 ± 0.310 | 16.50 ± 1.47 | 11.58 ± 1.10 |

TABLE 12

Variations of whole blood iron content and SF after treatment
n = 10

| Groups | Whole blood iron (µg/ml) 12 days | Whole blood iron (µg/ml) 18 days | SF (ng/ml) 12 days | SF (ng/ml) 18 days |
|---|---|---|---|---|
| High dosage of ferrous L-threonate | 5.567 ± 0.490 | 8.973 ± 0.952 | 13.81 ± 0.3 | 24.12 ± 0.77 |
| Middle dosage of ferrous L-threonate | 5.304 ± 0.594 | 8.879 ± 0.890 | 12.36 ± 0.21 | 22.91 ± 0.68 |
| Low dosage of ferrous L-threonate | 4.508 ± 0.235 | 6.384 ± 1.188 | 10.90 ± 0.75 | 18.70 ± 1.16 |
| Ferrous gluconate group | 5.450 ± 0.376 | 7.027 ± 0.799 | 12.12 ± 0.11 | 22.33 ± 1.33 |
| Ferrous fumarate group | 4.583 ± 0.794 | 6.446 ± 0.745 | 11.46 ± 0.71 | 19.67 ± 0.98 |
| Model group | 3.358 ± 0.286 | 5.077 ± 0.937 | 8.13 ± 0.44 | 13.87 ± 1.41 |

Results listed in table 10–12 showed that under the same ferrous dosage, ferrous L-threonate has better effects on treating IDA compared with both ferrous gluconate and ferrous fumarate.

EXPERIMENT 3

The Clinical Study of Ferrous L-threonate on Improving the Cases of IDA for Children Drugs: Ferrous L-threonate tablets, white color and 7.5 mg ferrous content and 30 mg vitamin C each tablet, was supplied by Beijing Juneng Asia-Pacific Life Science Research Center.

Subjects: Thirty school-age children aged from 8 to 13 years of Haerbin city of China.

Methods: Blood samples of 10 µl from ear and 5 ml from arm vein for each patient were collected for measurement.

(1) Measurement of RBC: 10 µl blood sample was added to 2 ml diluent and the mixture was shaken completely. One drop of this suspending solution taken by circle glass bar was poured into counting cell. RBC was countered through microscope by laying counting plate on the microstat.

(2) Measurement of HB: The ferric cyanide method was used to determine the HB. 10 µl ear blood sample was added to 5 ml acid diluent to obtain the completely mixed solution by shaking. HB was measured by SH hemoglobinometer manufactured by Huauang Instrument Company of Jianshu Province. Ferric cyanide was purchased from Medical Examination Institute of Shanghai.

(3) Measurement of FEP: To add 0.05 ml whole blood sample anticoagulated by heparin to 3.5 ml of acid anhydrous ethyl alcohol, the mixture was shaken for 5 min and then was centrifugalized with speed of 3000 r/min. The centrifugate of mixture was used for the measurement of fluorometric method (400 nm for exciting optical filter and 600 nm for emitting optical filter).

According to formula given below, the FEP can be calculated.

$$FEP(\mu g/L\ RBC) = 35 \times \frac{Fu}{PCV}$$

Where Fu and PCV represent fluorescence extent and hematocrit, respectively.

(4) Measurement of SF: SF reagent box was purchased from Tianjing Jiuding Biotechnology company and SN-682 radio-immune γ-ray counter was manufactured by Rihuan Instrument Company, Nuclear Medical Institute of Shanghai.

To centifugalized 2 ml whole blood sample, the upper solution was used for measurement of SF through the method of radio-immune competition-inhibition program.

Test steps:

(1) Determination of Anemia: Based on the standards of WHO and China investigation of prevention and treatment for IDA, Hb<120 g/L, FEP>500 µg/L, SF<16 µg/L and RBC<4 million/mm$^3$, together with the clinical examination, 39 males and 22 females were diagnosed as IDA patients (Hb<120 g/L) from 300 boys and 274 girls.

Among these 62 IDA patients, 30 children were randomly selected as treatment group of ferrous L-threonate.

Another 30 children with IDA were selected from another prime school with the same diagnosing standards and were established as control group.

(2) Intervention test: Child with IDA did usually not like activity, concentrated their attention difficultly and showed apathetic, sleepy, poor appetite and pale skin.

Observation time for treatment group and control group was 30 days period and during that period, there were no any intervention on children's activity and food.

(3) Dosages: Each child of treatment group was administered ferrous L-threonate tablets twice a day, one tablet each time. While normal control group was treated with placebo by the same method.

Results:

TABLE 13

Variations of Hb and FEP before and after treatment

| Groups | Before treatment ($\bar{x} \pm S$) | | After treatment ($\bar{x} \pm S$) | |
|---|---|---|---|---|
| | Hb (g/L) | Hb (g/L) | FEP (µg/L) | FEP (µg/L) |
| Treatment group | 104.8 ± 6.1 | 669.1 ± 72.0 | 120.4 ± 11.2 | 445.1 ± 80.9 |
| Control group | 102.8 ± 6.7 | 754.5 ± 76.4 | 103.6 ± 9.1 | 748.9 ± 85.5 |

TABLE 14

Variations of SF and RBC before and after treatment

| Groups | Before treatment ($\bar{x} \pm S$) | | After treatment ($\bar{x} \pm S$) | |
|---|---|---|---|---|
| | (µg/L) | RBC ($10^4/mm^3$) | SF (µg/L) | RBC ($10^4/mm^3$) |
| Treatment group | 12.45 ± 1.50 | 387 ± 6.67 | 17.01 ± 1.99 | 401.5 ± 12.4 |
| Control group | 12.0 ± 0.9 | 377 ± 9.7 | 12.7 ± 1.5 | 380 ± 8.8 |

The results of Hb, SF and RBC listed in table 13 and table 14 measured before and after treatment showed that the variations of each item for treatment group reaches the level of understandingly significant difference (P<0.01). Also, after 30 days of treatment by ferrous L-threonate, these variations of treatment group are significantly better compared with those of control group (P<0.01).

TABLE 15

Effectiveness of supplementation of ferrous L-threonate

| Groups | Hb > 120 g/L and ΔHb > 10 g/L (%) | ΔHb > 5 g/L (%) | No effectiveness (%) | Total (%) |
|---|---|---|---|---|
| Treatment group | 17 (56.7%) | 7 (23.3%) | 6 (20.0%) | 30 (100.0%) |
| Control group | 0 (0%) | 0 (0%) | 30 (100.0%) | 0 (100.0%) |

Thus, the effective rate of improving the case of IDA for children by ferrous L-threonate is as high as 80%.

EXAMPLE 1

Preparation of Ferrous L-threonate

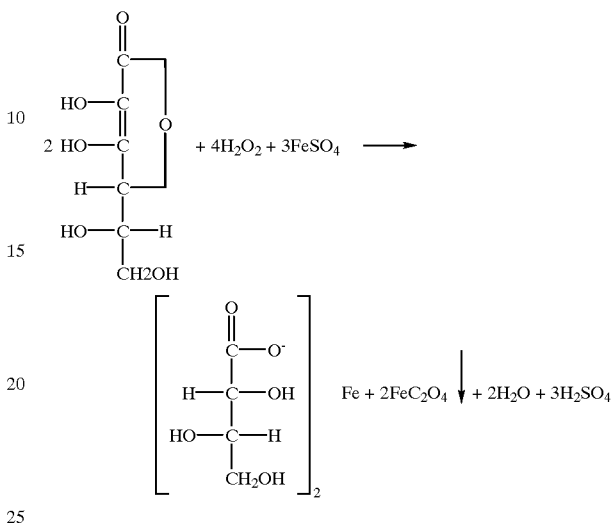

0.1 mol vitamin c was solved in 500 ml water distilled twice. The solution was adjusted to weak alkaline (pH=7–9) by 0.1 mol/L sodium hydroxide (NaOH) and the hydrogen peroxide ($H_2O_2$) of concentration 30% was added to it drop by drop in the condition of stirring. The mixture was kept for 20 min at about 10° C., and then treated with activated carbon, and heated at 80° C. to decompose the excess of hydrogen peroxide. When evolution of oxygen had ceased, the hot mixture was filtered, and the filtrate was cooled to room temperature for further processing. Under the protection of inert gas, for example, nitrogen gas ($N_2$), 0.15 mol ferrous sulfate ($FeSO_4.2H_2O$) was added to filtrate in a small portion gently. The reaction mixture was stirred two hours, the filtered and the filtrate was concentrated under diminished pressure. The pale green crystals that formed in the course of several hours were separated by filtration and finally were recrystallized twice from distilled water. The product obtained in this way was ferrous L-threonate with two crystal water molecules, $C_8H_{14}O_{10}Fe.2H_2O$.

Anal. Calc. For $C_8H_{14}O_{10}Fe.2H_2O$: C 26.52, H 5.01, Fe 15.42. Found: C 26.66, H 4.91, Fe 15.23.

When treating $Fe(C_4H_7O_5)_2.2H_2O$ at 10 mmHg diminished pressure and 50° C. temperature, the ferrous L-theronate with one crystal water molecule was obtained.

Anal. Calc. For $C_8H_{14}O_{10}Fe.H_2O$: C 27.91, H 4.69, Fe 16.23. Found: C 27.66, H 4.94, Fe 16.53.

Anhydrous ferrous L-threonate was prepared by drying $Fe(C_4H_7O_5)_2.H_2O$ at 5 mmHg diminished pressure and 120° C. temperature.

Anal. Calc. For $C_8H_{14}O_{10}Fe$: C 29.45, H 4.33, Fe 17.13. Found: C 29.11, H 4.39, Fe 17.60.

EXAMPLE 2

Composition of Ferrous L-threonate Tablet

| Composition for 1000 tablets: | |
|---|---|
| Ferrous L-threonate | 48.5 g |
| Vitamin C | 30 g |
| Mannitol | 180 g |
| Starch | 80 g |
| Magnesium stearate | right amount |
| Perfumery compound | right amount |

The components above were granlulated, dried and molded to obtain 1000 tablets of Ferrous L-threonate.

What is claimed is:

1. A compound having the formula of

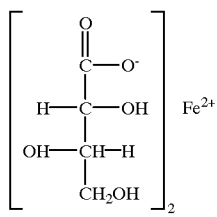

or hydrate thereof.

2. A pharmaceutical composition comprising a pharmaceutically effective amount of a compound having the formula

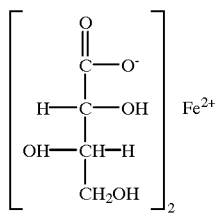

or a hydrate thereof and a pharmaceutically acceptable carrier.

3. The pharmaceutically composition according to claim 2, wherein said compound is present in an amount of about 10–90% by weight of the composition.

4. The pharmaceutical composition according to claim 1, further comprising vitamin C and/or vitamin $B^{12}$.

5. A method for treating anemia in a mammal, comprising administering to the mammal a pharmaceutically effective amount of a ferrous L-threonate compound having the formula

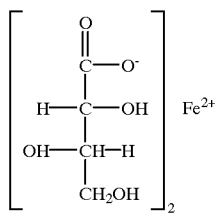

or a hydrate thereof.

6. The method according to claim 5, wherein the ferrous L-threonate compound is administered at a dosage of from about 0.01 to 1 gram per day.

7. The method of claim 5, wherein the anemia is nutritional iron-deficiency (hypoferric) anemia, blood-loss (hemorrhagic) anemia, or hemolytic anemia.

8. The method of claim 5, wherein the mammal is a human.

9. A method for supplying iron to a mammal, comprising administering to the mammal a pharmaceutically effective amount of a compound having the formula

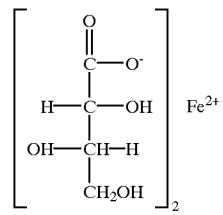

or a hydrate thereof.

10. A method for preventing anemia in a mammal, comprising administering to the mammal a pharmaceutically effective amount of a compound having the formula

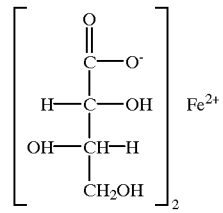

or a hydrate thereof.

11. A process for the preparation of a compound having the formula

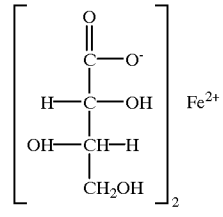

or a hydrate thereof, comprising reacting L-threonate acid with a ferrous compound selected from the group consisting of inorganic ferrous salts, ferrous oxides and ferrous hydroxides.

12. A process for preparing a compound having the formula

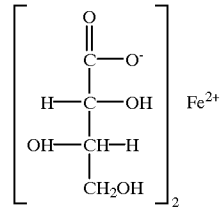

or a hydrate thereof, comprising:
reacting calcium L-threonate with an inorganic salt of ferrous under conditions so as to provide ferrous L-threonate.

* * * * *

UNITED STATES PATENT AND TRADEMARK OFFICE
CERTIFICATE OF CORRECTION

PATENT NO. : 6,313,170 B1 Page 1 of 1
DATED : November 6, 2001
INVENTOR(S) : Yu et al.

It is certified that error appears in the above-identified patent and that said Letters Patent is hereby corrected as shown below:

Column 15,
Line 45, "pharmaceutically" should read -- pharmaceutical --;
Line 48, "claim 1" should read -- claim 2 --;
Line 67, after "to" insert -- about --.

Column 16,
Line 46, "L-threonate" should read -- L-threonic --.

Signed and Sealed this

Second Day of July, 2002

*Attest:*

JAMES E. ROGAN
*Attesting Officer*     *Director of the United States Patent and Trademark Office*